US009897757B2

(12) United States Patent
Ronen et al.

(10) Patent No.: US 9,897,757 B2
(45) Date of Patent: Feb. 20, 2018

(54) FLUORESCENCE EXCITATION ILLUMINATION FIBER

(71) Applicant: Visionsense Ltd., Petah Tikva (IL)

(72) Inventors: Udi Ronen, Kfar Saba (IL); Martin Abraham, Hod Hasharon (IL); Nadav Haresh, Ramat Raziel (IL); Alex Chanin, Holland, PA (US); Ofer Braude, Ramat Gan (IL)

(73) Assignee: VISIONSENSE LTD., Petah Tikva (IL)

( * ) Notice: Subject to any disclaimer, the term of this patent is extended or adjusted under 35 U.S.C. 154(b) by 0 days.

(21) Appl. No.: 14/849,336

(22) Filed: Sep. 9, 2015

(65) Prior Publication Data

US 2016/0077280 A1    Mar. 17, 2016

(30) Foreign Application Priority Data

Sep. 11, 2014 (IL) .......................... 234605

(51) Int. Cl.

| | |
|---|---|
| G02B 6/26 | (2006.01) |
| A61B 1/00 | (2006.01) |
| A61B 1/04 | (2006.01) |
| A61B 1/07 | (2006.01) |
| G02B 23/24 | (2006.01) |
| A61B 1/06 | (2006.01) |
| G02B 5/02 | (2006.01) |

(52) U.S. Cl.
CPC .......... *G02B 6/262* (2013.01); *A61B 1/00096* (2013.01); *A61B 1/00167* (2013.01); *A61B 1/043* (2013.01); *A61B 1/0638* (2013.01); *A61B 1/07* (2013.01); *G02B 23/2469* (2013.01); *A61B 1/0017* (2013.01); *G02B 5/02* (2013.01)

(58) Field of Classification Search
CPC ................................. G02B 6/26; G02B 6/262
USPC .......................................................... 385/27
See application file for complete search history.

(56) References Cited

U.S. PATENT DOCUMENTS

| 4,465,335 A | * | 8/1984 | Eppes | ................. G02B 6/2804 |
|---|---|---|---|---|
| | | | | 359/900 |
| 5,452,723 A | * | 9/1995 | Wu | ...................... A61B 5/0059 |
| | | | | 250/339.01 |

(Continued)

FOREIGN PATENT DOCUMENTS

| EP | 2 502 549 A1 | 9/2012 |
|---|---|---|
| EP | 2792933 A1 | 10/2014 |
| WO | 2013/089102 A1 | 6/2013 |

OTHER PUBLICATIONS

Extended European Search Report issued in corresponding European Application No. 15184897.5, dated Dec. 17, 2015.

(Continued)

*Primary Examiner* — Kaveh C Kianni
(74) *Attorney, Agent, or Firm* — Merchant & Gould P.C.

(57) ABSTRACT

Fluorescence imaging illumination fiber including a first fiber, a second fiber, and a diffuser, the second fiber concentrically enfolding the first fiber, the diffuser is coupled at the end of the first fiber and the second fiber, the first fiber having a first angular output, the second fiber having a second angular output, the diffuser increasing the first angular output by a first value and increasing the second angular output by a second value, the first value exceeding the second value.

12 Claims, 3 Drawing Sheets

(56) References Cited

U.S. PATENT DOCUMENTS

| | | | | |
|---|---|---|---|---|
| 5,534,386 | A * | 7/1996 | Petersen | G02B 5/0252 264/1.31 |
| 5,684,908 | A * | 11/1997 | Kross | G02B 6/4298 385/125 |
| 5,896,483 | A * | 4/1999 | Wojcik | G02B 6/032 385/125 |
| 6,272,269 | B1 * | 8/2001 | Naum | G02B 6/0026 362/551 |
| 2004/0073120 | A1 * | 4/2004 | Motz | A61B 5/0075 600/478 |
| 2012/0053420 | A1 * | 3/2012 | Kasamatsu | A61B 1/0638 600/182 |
| 2012/0101348 | A1 * | 4/2012 | Yamaguchi | A61B 1/00009 600/317 |
| 2012/0245420 | A1 * | 9/2012 | Yoshida | A61B 1/00117 600/178 |
| 2013/0060087 | A1 * | 3/2013 | Yoshida | A61B 1/00045 600/112 |
| 2014/0293641 | A1 * | 10/2014 | Ito | A61B 1/00117 362/553 |
| 2014/0293651 | A1 * | 10/2014 | Ito | A61B 1/0669 362/613 |
| 2015/0309249 | A1 * | 10/2015 | Murshid | H04B 10/2581 398/55 |
| 2015/0316721 | A1 * | 11/2015 | Grossman | G02B 6/4203 385/27 |

OTHER PUBLICATIONS

"Light Shaping Diffusers, Technical Data Sheet", Luminit: Shaping Light as Needed, http://www.luminitco.com/sites/default/files/LSD_Tech_Datasht_5_21_12_lo_0.pdf, May 21, 2012, 2 pgs.

* cited by examiner

FLUORESCENCE EXCITATION ILLUMINATION FIBER

This application claims benefit of Serial No. 234605, filed 11 Sep. 2014 in Israel and which application is incorporated herein by reference. To the extent appropriate, a claim of priority is made to the above disclosed application.

FIELD OF THE DISCLOSED TECHNIQUE

The disclosed technique relates to multimode fiber, in general, and to methods and systems for transmitting two light wavelengths via a single fiber, such that the output beam field of view of a first transmitted wavelength is similar to the output beam field of view of a second transmitted wavelength, in particular.

BACKGROUND OF THE DISCLOSED TECHNIQUE

Fluorescence imaging is employed for imaging subcutaneous tissues. The fluorescence imager detects fluorescence light emitted from a fluorescence agent that is excited by appropriate illumination. For example, a fluorescent endoscope is an imaging system for imaging internal blood flow, visible through tissue, by promoting fluorescence radiation from a fluorescent dye added to the flowing blood. The endoscope can be employed, for example, during surgery for visualizing the blood flow, and for evaluating tissue perfusion and vessel patency.

Light guides for providing excitation illumination to fluorescence imaging systems are known in the art. Reference is now made to EP Patent Application Publication Number EP2502549A1, to Koji et al., and entitled "Endoscope Apparatus". This publication describes an endoscope having a light guiding portion that guides the light output from a light source (i.e., fluorescence excitation light source). The light guiding portion is equipped with a diffusing portion at the output end thereof. The diffuser is designed to diffuse the output excitation light for preventing the light from causing damage to the eye of the user.

Reference is now made to a light shaping diffusers technical data sheet of Luminit Co. This publication describes a diffuser that modifies the angular output of an incoming light beam in accordance with the angular output of the incoming light beam in accordance with the angular output of the incoming beam and with the diffuser angle.

Reference is now made to US Patent Application Publication Number 2013/0060087 to Yoshida, and entitled "Rigid Scope Apparatus". This publication is directed at a rigid scope apparatus including an illumination fiber. The illumination fiber contains a white light fiber bundle and a near infrared fiber bundle. The white light fiber bundle and the near infrared fiber bundle can be concentrically formed within the illumination fiber. The rigid scope apparatus may further include a white light diffusion section for diffusing the white light, and an infrared diffusion section for diffusing the near infrared light.

SUMMARY OF THE DISCLOSED TECHNIQUE

It is an object of the disclosed technique to provide a fluorescence imaging illumination fiber, which overcomes the disadvantages of the prior art. In accordance with the disclosed technique, there is thus provided a fluorescence imaging illumination fiber system. The illumination fiber system includes a first fiber, a second fiber, and a diffuser. The second fiber concentrically enfolds the first fiber. The first fiber is designed to transmit a first beam. The first beam has a first angular output at an output of the first fiber. The second fiber is designed to transmit a second beam. The second beam has a second angular output at an output of the second fiber. The diffuser is coupled with the output of the first fiber and with the output of the second fiber. The diffuser increases the first angular output of the first fiber by a first value, and increasing the second angular output of the second fiber by a second value. The first value exceeds the second value.

BRIEF DESCRIPTION OF THE DRAWINGS

The disclosed technique will be understood and appreciated more fully from the following detailed description taken in conjunction with the drawings in which:

FIG. 1 is a schematic illustration of a fluorescence imaging system, constructed and operative in accordance with an embodiment of the disclosed technique;

FIG. 2 is a schematic illustration of a fluorescence image detection system, constructed and operative in accordance with another embodiment of the disclosed technique;

FIGS. 3A and 3B are schematic illustrations of a fluorescence excitation illumination fiber, constructed and operative in accordance with a further embodiment of the disclosed technique; and FIG. 4 is a schematic illustration of a graph depicting the diffused angular output as a function of the source angular output for the diffuser described herein above in FIGS. 3A and 3B, operative in accordance with yet another embodiment of the disclosed technique.

DETAILED DESCRIPTION OF THE EMBODIMENTS

In order to provide enhanced illumination for a fluorescence device it is advantageous to provide both visible and fluorescence excitation light into the surgical field. This allows acquisition and display of both fluorescence and normal (i.e. visible) light images. The fluorescence and visible light images can then be displayed to the user or may be superimposed (i.e. fused together) to provide enhanced visualization (e.g. observation of blood flow in tissue being operated on). In situations where both fluorescence excitation light and visible observation light sources are necessary, the output angles of the two light sources must be matched to each other and to the required Field Of View (FOV) of the system. This is often difficult because the fluorescence excitation light may be generated by a relatively small angle source such as a laser diode while the visible observation light may be generated by relatively large angle sources such as Xenon or LED. Therefore, the light guide of the disclosed technique is designed such that the output angles of the sources (i.e., fluorescence and visible) are matched to each other and to the required FOV of the respective imaging system.

The disclosed technique overcomes the disadvantages of the prior art by providing a fluorescence excitation illumination fiber including a first fiber, a second fiber concentrically enfolding the first fiber, and a diffuser coupled with the output of both fibers. That is, the illumination fiber actually consists of two concentric fibers. The first fiber (i.e., the inner fiber) is designed to transmit a first beam (e.g., fluorescence excitation light) having a first angular output. The second fiber (i.e., the outer fiber) is designed to transmit a second beam (e.g., visible observation light) having a second angular output. The diffuser increases the first angular output of the first fiber by a first value, and increases the second angular output of the second fiber by a second value. The first value exceeds the second value, such that at the output of the illumination fiber, the FOV of the first beam is similar to that of the second beam. In other words, the diffuser increases the beam divergence of the inner fiber more than it increase the beam divergence of the outer fiber, such that after the diffuser, the beam divergence of the inner fiber corresponds to that of the outer fiber.

Figure 01:
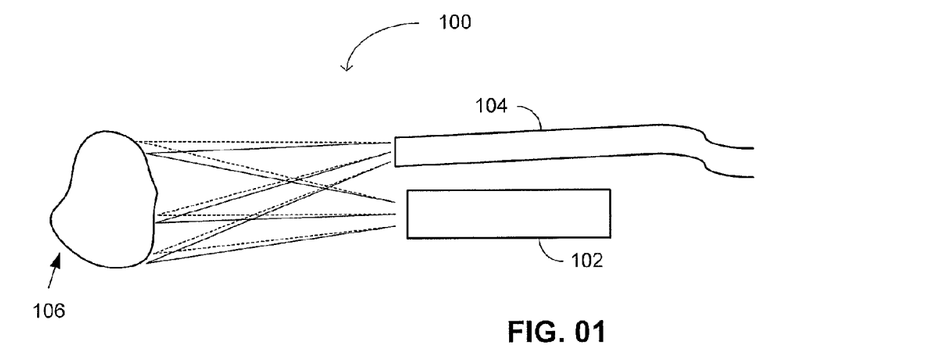

Reference is now made to FIG. 1, which is a schematic illustration of a fluorescence imaging system, generally referenced 100, constructed and operative in accordance with an embodiment of the disclosed technique. Fluorescence imaging system 100 includes an image detection system 102 and an illumination fiber 104. Fluorescence imaging system 100 acquires images of an object 106.

Detection system 102 detects fluorescent emissions emitted from object 106, and produces accordingly a fluorescent image of object 106. Detection system 102 further detects a visible image of object 106 by detecting visible light reflected from object 106. The structure and components of detection system 102 are further elaborated herein below with reference to FIG. 2.

Illumination fiber 104 illuminates object 106. In particular, illumination fiber 104 is a multimode fiber transmitting white light, and transmitting a fluorescence excitation light that excites fluorescent emissions from a fluorescent agent in object 106 (e.g., Near Infrared light—NIR). For imaging object 106 fully, the FOV of both of the white light beam and the excitation light beam should fill or exceed that of detection system 102. Put another way, on object 106, the beam diameter of both the white light and the NIR light should fill or exceed the FOV of detection system. Otherwise, an area of object 106 which is not illuminated with excitation light, would not emit fluorescent light even if it includes a fluorescent agent. Thereby, that area would not be captured in the fluorescent image, which might lead to clinical misinterpretations. Similarly, an area of object 106 which would not be illuminated by visible light—would not be imaged in the visible image.

Additionally, the portion of the illumination beam FOV that exceeds the FOV of the detection system is not employed and is thus wasted. Therefore, for reducing waste, the FOV of the illuminations beams (i.e., both the white light beam and the excitation light beam) should not exceed that of the detection system by a large factor. The structure and components of illumination fiber 104 are further elaborated herein below with reference to FIGS. 3A and 3B.

Figure 02:
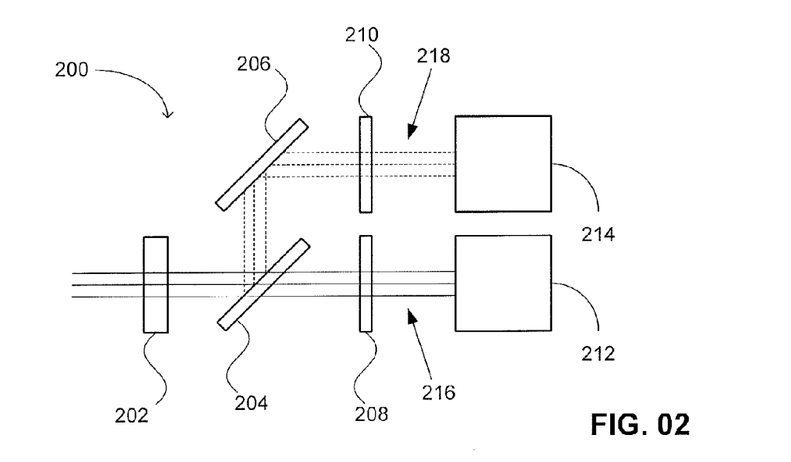

Reference is now made to FIG. 2, which is a schematic illustration of an exemplary fluorescence image detection system, generally referenced 200, constructed and operative in accordance with another embodiment of the disclosed technique. Detection system 200 includes an excitation light filter 202, a dichroic mirror 204, a mirror 206, a short pass filter 208, a long pass filter 210, a visible light camera 212 and an IR light camera 214.

Excitation light filter 202 is located on the object side of dichroic mirror 204 and is optically coupled therewith. Dichroic mirror 204 is further optically coupled with a visible light camera 212 via short pass filter 208, and with IR camera 214 via mirror 206 and long pass filter 210.

Excitation light filter 202 blocks (or at least attenuates) reflected excitation light, and admits fluorescence light 218 and reflected visible light 216 into detection system 200. Dichroic mirror 204 reflects IR light 218 (i.e., the fluorescence emissions light) while enabling visible light 216 (i.e., the reflected white light) to pass therethrough. Visible camera 212 detects a visible image of the object (e.g., object 106 of FIG. 1), while IR camera 214 detects the fluorescence image of the object.

Figure 03A:
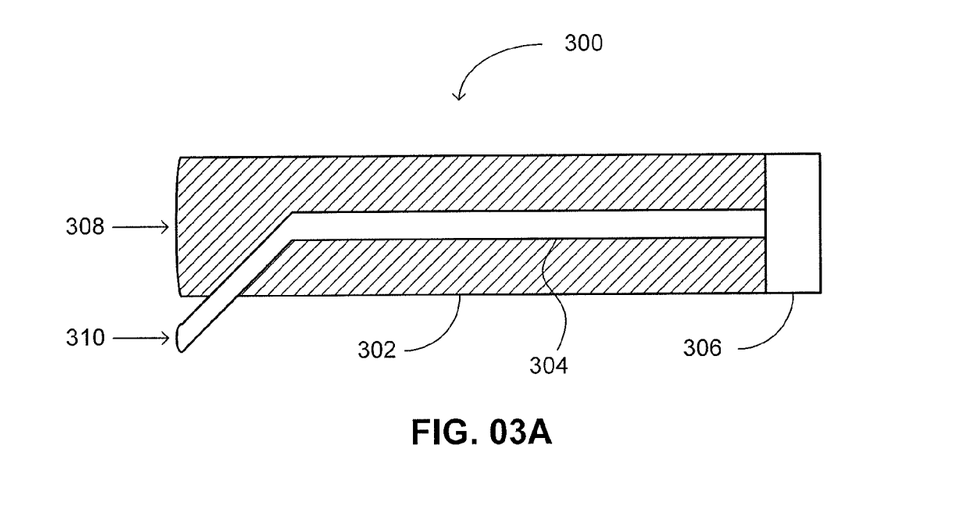
Figure 03B:
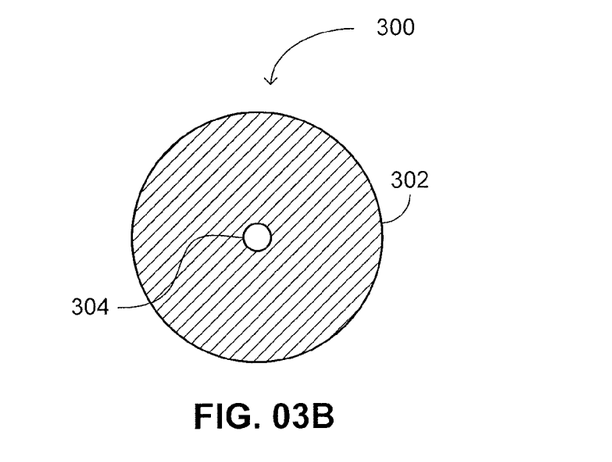

Reference is now made to FIGS. 3A and 3B, which are schematic illustrations of a fluorescence excitation illumination fiber, generally referenced 300, constructed and operative in accordance with a further embodiment of the disclosed technique. FIG. 3A depicts a side view cross section of fiber 300, and FIG. 3B depicts a front view cross section of fiber 300.

Fiber 300 includes a white light fiber 302 (or a white light portion 302), a fluorescence excitation fiber 304 (or a fluorescence portion 304), a diffuser window 306, a white light input port 308, and a fluorescence light input port 310. Fluorescence fiber 304 is enclosed within white light fiber 302 concentrically with white light fiber 302 (i.e., at the center of), or close to the center thereof. Thus, fluorescence fiber 304 and white light fiber 302 form together a concentric fiber. Diffuser window 306 is coupled with the distal end of both white light fiber 302 and fluorescence fiber 304. White light input port 308 is coupled with the proximal end of white light fiber 302. Fluorescence light input port 310 is coupled with the proximal end of fluorescence fiber 304.

Fiber 300 is a multimode fiber which allows transmission of both white light and fluorescence excitation light. The white light is provided by a white light source that is coupled to fiber 300 via white light port 308. White light travels through white light fiber 302 and is diffused by diffuser window 306. The fluorescence excitation light (i.e., the fluorescence light) is coupled with fiber 300 via fluorescence light port 310. The fluorescence excitation light is provided by a fluorescence light source that is coupled to fiber 300 via fluorescence light port 310. Fluorescence light travels through fluorescence fiber 304 and is diffused by diffuser window 306.

Fluorescence fiber 304 can be, for example, a thin silica fiber (e.g., having diameter ranging between 400 micrometer-800 micrometer) effective for transmission of fluorescence light generated, for example, by a laser diode. Light fiber 302 is glass fiber effective of transmission of visible light with relatively larger output angle (e.g., Numerical Aperture of 0.55) and relatively large diameter (e.g., ranging between 3.5 millimeter and 4.8 millimeter). In this configuration, the relatively small diameter (e.g., 400 micrometer) of the fluorescence fiber 304 does not significantly diminish the light output of the relatively large diameter (e.g., 4.5 millimeter) of white light fiber 302. The net effect is that the light guide (i.e., fiber 300) provides high quality fluorescence excitation light to the field while preserving the white light output power of a common fiber optic light guide (e.g., 4.5 millimeter endoscope light guide). It is also notable that the fluorescence excitation light fiber is positioned in the center of fiber 300 to allow good fluorescence light coupling to small diameter endoscopes.

Diffuser window 306 diffuses incoming light thereby enlarging the FOV of the diffused beam. For example, diffuser 306 can increase the beam angle according to the following formula [1]:

$$\text{output} = \sqrt{(\text{source})^2 + (\text{diffuser})^2}$$

Wherein the output angle equals the square root of the sum of the square of the source angle and the square of the diffuser angle. For example, the diffuser angle can range between 10° and 95° (FWHM).

In accordance with the example set forth in formula [1], and for a diffuser angle of approximately 60°, in case the output angle of white light fiber 302 is 65° and the output angle of fluorescence fiber 304 is 25°, the output angle of white light from diffuser 306 would be approximately 85° and the output angle of fluorescence light from diffuser 306 would be approximately 65°. Thereby, the angular output (or the FOV) of the fluorescence light illumination beam is increased more than the angular output (or the FOV) of the white light beam. Thus, fiber 300 can provide multimode illumination beams of similar FOVs. It is noted that in the example set forth herein, the FOV of the effective multimode illumination (i.e., both white light and fluorescence light) would be 65°, and the excess white light exceeding that output angle would not be employed for illuminating the imaged object.

This modification of the incoming beam angle is useful for matching the output angle of the illumination beam with the FOV of the imaging system. The modification is also useful for matching the output angle of the excitation light (frequently generated by a laser diode) to the angle of the visible light (frequently generated by an LED or Xenon light source) in use cases where both visible light and excitation light are used.

In the example set forth herein above in FIGS. 3A and 3B, the multimode fiber transmits a white light beam and a fluorescence light beam. Alternatively, the multimode fiber of the disclosed technique can transmit any two light beams of any wavelength, such as an ultraviolet beam and a green beam, or a blue beam and a red beam. The two beams travel through different portions of the fiber and are diffused at the output of the fiber by the diffuser, such that the FOVs of the beams become substantially similar (or at least more similar than the original FOVs of the beams prior to diffusion).

In accordance with another alternative embodiment of the disclosed technique, the multimode fiber includes more than two concentric portions. For example the multimode fiber includes four concentric portions (enfolding each other) for transmitting four separate beams. The beams are diffused at the output of the fiber, and the output beam angles are selected such that the respective FOV of the most inner beam is increased by the largest factor and the FOV of the outermost beam is increased by the least factor. That is, the beams are diffused such that the angular output of each beam is increased in an escalating manner from the inner beam to the outer beam. Thereby, FOVs of the diffused beams better correspond to each other.

Figure 04:
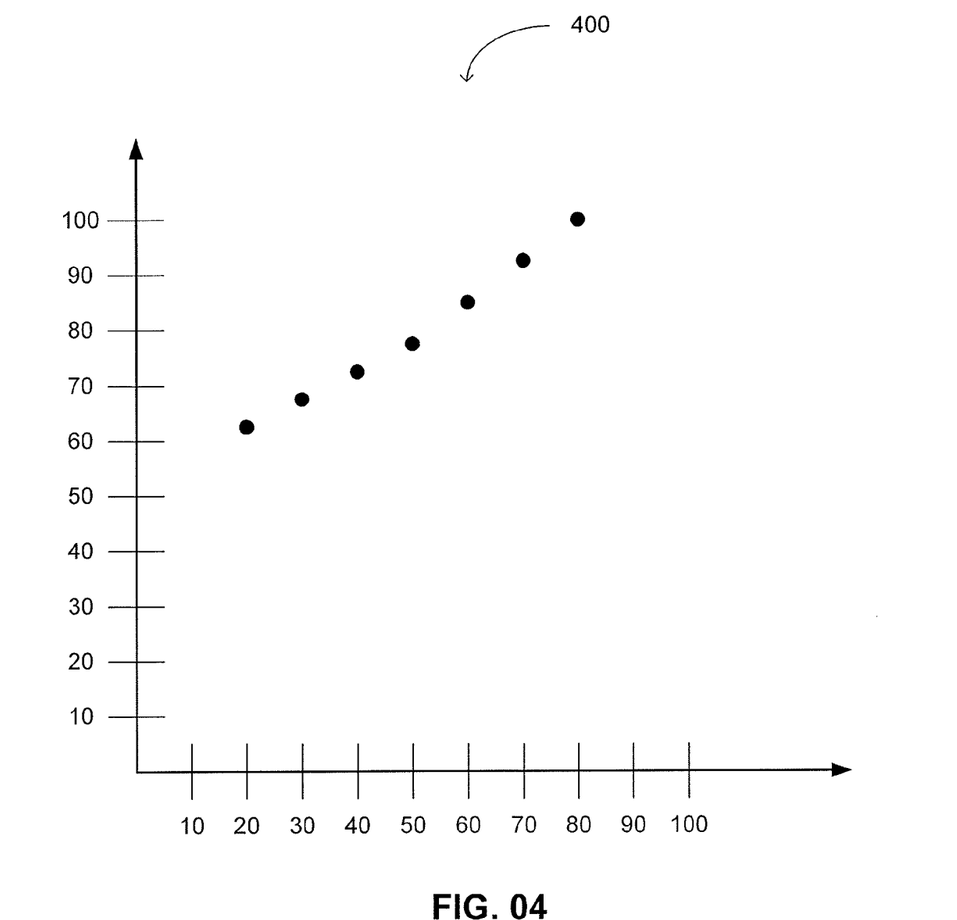

Reference is now made to FIG. 4, which is a schematic illustration of a graph, generally referenced 400, depicting the diffused angular output as a function of the source angular output for the diffuser described herein above in FIGS. 3A and 3B, operative in accordance with yet another embodiment of the disclosed technique. Graph 400 visually depicts equation [1] detailed herein above. The Y axis represents the diffused angular output and the X axis depicts the source angular output. As can be seen in FIG. 4, the diffused angular output has a minimum of 60 degrees, which is given by the diffuser angle, even for negligent source output angles. Additionally, the diffused angular output increases more slowly than the source angular output. Thereby, the diffuser increases the relatively small angular output of the fluorescence source (e.g., 25°) by much larger factor than it increases the relatively large angular output of the visible source (e.g., 65°). In this manner, the diffused angular output of the fluorescence beam is made similar to the diffused angular output of the visible beam.

It is noted that the imaging system described herein above with reference to FIG. 2, serves only an example of a fluorescence imaging system, which employs the illumination fiber of the disclosed technique. Generally, the illumination fiber of the disclosed technique can be employed for any imaging system employing two illumination beams produced by two sources. Moreover, the illumination fiber of the disclosed technique can be employed wherever, there is a need to transmit two light beams, and to project the light beams at the distal output port such that both beams have substantially similar angular outputs and FOVs.

As can be seen in FIG. 4, the diffusion is non-linear. In particular, the diffusion factor decreases as the angular output of the source increases. In the example set forth in FIG. 3A the output of diffuser 306 is given by equation [1] as detailed there. Alternatively, other non-linear diffusers can be employed. Generally, the system of the disclosed technique employs a first source having a first angular output and a second source having a second angular output. The first angular output is smaller than the second angular output. The system of the disclosed technique can employ any diffuser that diffuses the first source (having the smaller angular output) by a larger factor than the diffusion of the second source (having the larger angular output).

It will be appreciated by persons skilled in the art that the disclosed technique is not limited to what has been particularly shown and described hereinabove. Rather the scope of the disclosed technique is defined only by the claims, which follow.

The invention claimed is:

1. Fluorescence imaging illumination system comprising:
an image detection system; and
an illumination fiber, said illumination fiber comprising:
a fluorescent light fiber designed to transmit a first beam of light having a first wavelength and a first angular output, said fluorescent light fiber comprising a fluorescent light input port;
a visible light fiber designed to transmit a second beam of light having a second wavelength and a second angular output which is larger than said first angular output of said fluorescent light fiber, said visible light fiber comprising a visible light input port; and
a non-linear diffuser coupled with said output of said fluorescent light fiber and with said output of said visible light fiber, having a diffusion factor which decreases as an angular output of a source beam increases for simultaneously diffusing said first beam and said second beam so that said first angular output of said fluorescent light fiber is increased by a first value, and said second angular output of said visible light fiber is increased by a second value, said first value exceeding said second value;
wherein a difference between said increased first angular output of said fluorescent light fiber and said increased second angular output of said visible light fiber is reduced by said non-linear diffuser bringing said first angular output and said second angular output closer to each other in value;
wherein said fluorescent light fiber is enclosed concentrically with said visible light fiber;
wherein a fluorescence excitation light source is coupled with said fluorescent light input port for generating said first beam of light and a visible light source is coupled with said visible light input port for generating said second beam of light; and
wherein said first wavelength corresponds to fluorescent light and said second wavelength corresponds to visible light.

2. The fluorescence imaging illumination system of claim 1, wherein said non-linear diffuser increasing each of said first angular output and said second angular output in accordance with the following equation:
$$\text{output} = \sqrt{(\text{source})^2 + (\text{diffuser})^2}.$$

3. The fluorescence imaging illumination system of claim 1, wherein a diameter of said fluorescent light fiber is between 400 micrometers and 800 micrometers.

4. The fluorescence imaging illumination system of claim 1, wherein a diameter of said visible light fiber is between 3.5 millimeters and 4.8 millimeters.

5. The fluorescence imaging illumination system of claim 1, wherein said fluorescent light fiber is a silica fiber.

6. The fluorescence imaging illumination system of claim 1, wherein said visible light fiber comprises a glass fiber.

7. The fluorescence imaging illumination system of claim 1, wherein said fluorescent light is near infrared light.

8. Fluorescence imaging illumination system comprising:
an image detection system; and
an illumination fiber,
said illumination fiber comprising:
a first fiber designed to transmit a first beam of light having a first wavelength and a first angular output, said first fiber comprising a first light input port;
a second fiber designed to transmit a second beam of light having a second wavelength and a second angular output which is larger than said first angular output of said first fiber, said second fiber comprising a second light input port; and
a non-linear diffuser, coupled with said output of said first fiber and with said output of said second fiber, having a diffusion factor which decreases as an angular output of a source beam increases, for simultaneously diffusing said first beam of light and said second beam of light such that said first angular output of said first fiber is increased by a first value and said second angular output of said second fiber is increased by a second value, said first value exceeding said second value,
wherein a difference between said increased angular outputs of said first fiber and said second fiber is reduced by said non-linear diffuser bringing said angular outputs closer to each other in value;
wherein said first fiber is enclosed concentrically with said second fiber;
wherein a first light source is coupled with said first light input port for generating said first beam of light and a second light source is coupled with said second light input port for generating said second beam of light; and
wherein said first wavelength and said second wavelength are different.

9. The fluorescence imaging illumination system of claim 8, wherein said second wavelength corresponds to visible light.

10. The fluorescence imaging illumination system of claim 8, wherein said first wavelength corresponds to fluorescent light.

11. The fluorescence imaging illumination system of claim 10, wherein said fluorescent light is near infrared light.

12. Fluorescence imaging illumination system comprising:
an image detection system; and
an illumination fiber,
said illumination fiber comprising:
a fluorescent light fiber designed to transmit a first beam of light having a first wavelength and a first angular output, said fluorescent light fiber comprising a fluorescent light input port;
a visible light fiber designed to transmit a second beam of light having a second wavelength and a second angular output which is larger than said first angular output of said first fiber, said visible light fiber comprising a visible light input port; and
a non-linear diffuser, coupled with said output of said first fiber and with said output of said second fiber, having a diffusion factor which decreases as an angular output of a source beam increases, for simultaneously diffusing said first beam of light and said second beam of light such that said first angular output of said fluorescent light fiber is increased by a first value and said second angular output of said visible light fiber is increased by a second value, said first value exceeding said second value;
wherein a difference between said increased angular outputs of said fluorescent light fiber and said visible light fiber is reduced by said non-linear diffuser bringing said angular outputs closer to each other in value;
wherein a fluorescence excitation light source is coupled with said fluorescent light input port for generating said first beam of light and a visible light source is coupled with said visible light input port for generating said second beam of light; and
wherein said first wavelength corresponds to fluorescent light and said second wavelength corresponds to visible light wherein the first fiber and the second fiber are optical fibers.

* * * * *

UNITED STATES PATENT AND TRADEMARK OFFICE
CERTIFICATE OF CORRECTION

PATENT NO.          : 9,897,757 B2                                     Page 1 of 2
APPLICATION NO.     : 14/849336
DATED               : February 20, 2018
INVENTOR(S)         : Ronen et al.

It is certified that error appears in the above-identified patent and that said Letters Patent is hereby corrected as shown below:

In the Specification

Column 1, Line 11: "multimode fiber," should read --multimode fibers,--

Column 1, Line 42: "light shaping diffusers" should read --light shaping diffuser--

Column 1, Line 50: "publication is directed at a" should read --publication is directed to a--

Column 1, Line 67: "a second fiber, and a diffuser." should read --a second fiber and a diffuser.--

Column 2, Line 9: "a first value, and increasing the second angular output" should read --a first value and increases the second angular output--

Column 2, Line 53: "as Xenon or LED." should read --as a Xenon light source or an LED.--

Column 3, Line 29: "(e.g., Near Infrared light" should read --(e.g., near infrared light--

Column 3, Line 40: "visible light--would not" should read --visible light would not--

Column 3, Line 34: "FOV of detection system." should read --FOV of the detection system.--

Column 3, Line 45: "the FOV of the illuminations beams" should read --the FOV of the illumination beams--

Column 3, Line 60: "optically coupled with a" should read --optically coupled with--

Column 4, Lines 38-39: "between 400 micrometer-800 micrometer)" should read --between 400 micrometers – 800 micrometers)--

Signed and Sealed this
Seventeenth Day of April, 2018

Andrei Iancu
*Director of the United States Patent and Trademark Office*

CERTIFICATE OF CORRECTION (continued)
U.S. Pat. No. 9,897,757 B2

Column 4, Line 41: "is glass fiber effective of transmission of" should read --is a glass fiber effectively transmitting--

Column 4, Lines 42-44: "with relatively larger output angle (e.g., Numerical Aperture of 0.55) and relatively large diameter (e.g., ranging between 3.5 millimeter and 4.8 millimeter)." should read --with a relatively larger output angle (e.g., Numerical Aperture of 0.55) and a relatively large diameter (e.g., ranging between 3.5 millimeters and 4.8 millimeters).--

Column 4, Lines 45-46: "400 micrometer) of the fluorescence fiber" should read --400 micrometers) of fluorescence fiber--

Column 4, Line 48: "millimeter) of white light" should read --millimeters) of white light--

Column 4, Line 52: "millimeter endoscope light guide)." should read --millimeters endoscope light guide).--

Column 4, Line 62: "Wherein" should read --wherein--

Column 4, Line 65: "and 95° (FWHM)." should read --and 95° (full width at half maximum-FWHM).--

Column 5, Line 41: "is increased by the least factor." should read --is increased by the smallest factor.--

Column 5, Line 60: "by much larger" should read --by a much larger--

Column 5, Lines 66-67: "with reference to FIG. 2, serves only an example of a fluorescence imaging system, which employs" should read --with reference to FIG. 2 serves only as an example of a fluorescence imaging system which employs--

Column 6, Line 5: "wherever, there is" should read --wherever there is--